United States Patent [19]

Gleason et al.

[11] Patent Number: 5,565,480

[45] Date of Patent: Oct. 15, 1996

[54] SUBSTITUTED HISTIDINES

[75] Inventors: John G. Gleason, Downingtown, Pa.; Judith Hempel, Cardiff, Calif.; David T. Hill, North Wales, Pa.; James Samanen; Joseph Weinstock, both of Phoenixville, Pa.

[73] Assignee: SmithKline Beecham Corporation, Philadelphia, Pa.

[21] Appl. No.: 434,333

[22] Filed: May 2, 1995

Related U.S. Application Data

[62] Division of Ser. No. 965,370, Dec. 19, 1993, Pat. No. 5,441,081, which is a continuation of Ser. No. 545,253, Jun. 28, 1990, abandoned.

[51] Int. Cl.$^6$ .................... A61K 31/415; C07D 233/70; C07D 233/84; C07D 233/64

[52] U.S. Cl. .................... 514/381; 514/398; 548/324.1; 548/251

[58] Field of Search ................ 548/324.1, 251; 514/398, 381

[56] References Cited

U.S. PATENT DOCUMENTS 5,234,917  8/1993  Finkelstein et al. .................... 514/397
5,387,601  2/1995  Hill .................................... 514/397
5,444,081  8/1995  Gleason et al. ...................... 514/399

*Primary Examiner*—Johann Richter
*Assistant Examiner*—Laura R. Cross
*Attorney, Agent, or Firm*—Mary E. McCarthy; Stephen Venetianer; Edward T. Lentz

[57] ABSTRACT

Angiotensin II receptor antagonists having the formula:

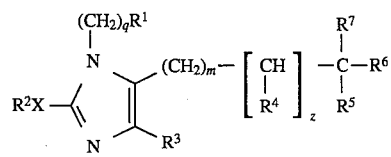

which are useful in regulating hypertension and in the treatment of congestive heart failure, renal failure, and glaucoma, pharmaceutical compositions including these antagonists, and methods of using these compounds to produce angiotensin II receptor antagonism in mammals.

8 Claims, No Drawings

SUBSTITUTED HISTIDINES

This is a divisional of application Ser. No. 07/965,370, filed Dec. 19, 1993 now U.S. Pat. No. 5,444,081 which is a continuation of application Ser. No. 07/545,253, filed Jun. 28, 1990 now abandoned.

The present invention relates to new substituted histidines which are angiotensin II receptor antagonists and are useful in regulating hypertension induced or exacerbated by angiotensin II and in the treatment of congestive heart failure, renal failure, and glaucoma. This invention also relates to pharmaceutical compositions containing substituted histidines and methods for using these compounds as antagonists of angiotensin II, as anti-hypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, stimulates the release of aldosterone from the adrenal cortex. Therefore, the renin-angiotensin system, by virtue of its participation in the control of renal sodium handling, plays an important role in cardiovascular homostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application Number 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure, glaucoma, and other disorders attributed to the actions of AII. When compounds of this invention are administered to mammals, the elevated blood pressure due to AII is reduced and other manifestations based on AII intercession are minimized and controlled. Compounds of this invention is also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

U.S. Pat. No. 4,340,598 discloses substituted imidazol-5-yl alkanoic acids, and amido and lower-alkyl ester derivatives thereof, of the formula:

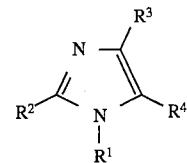

wherein $R^1$ is lower alkyl or phenyl$C_{1-2}$ alkyl optionally substituted with halogen or nitro; $R^2$ is lower alkyl, cycloalkyl, or phenyl optionally substituted; one of $R^3$ and $R^4$ is $-(CH_2)_nCOR^5$, where $R^5$ is amino, lower alkoxy or hydroxy and n is 0–2, and the other of $R^3$ and $R^4$ is hydrogen or halogen. Examples include 1-benzyl-2-n-butyl-4-chloroimidazole-5-acetamide and 1-benzyl-2-n-butyl-5-chloroimidazole-4-acetic acid.

U.S. Pat. No. 4,355,040 discloses substituted 1-benzylimidazol-5-yl acetic acid derivatives having the formula:

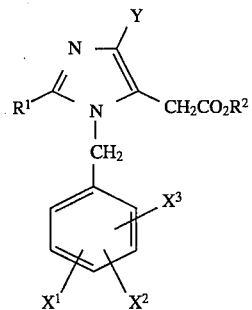

wherein $R^1$ is lower alkyl, cycloalkyl, or phenyl optionally substituted; $X^1$, $X^2$ and $X^3$ are each hydrogen halogen nitro, amino, lower alkyl, lower alkoxy, benzyloxy, or hydroxy; Y is halogen and $R^2$ is hydrogen or lower alkyl. A compound specifically disclosed is 1-(2-chlorobenzyl)-2-n-butyl-4-chloro-imidazole-5-acetic acid.

European Patent Application 103,647 discloses substituted 1-benzyl-2-phenyl-4-chloroimidazol-5-yl acetic acid derivatives of the formula:

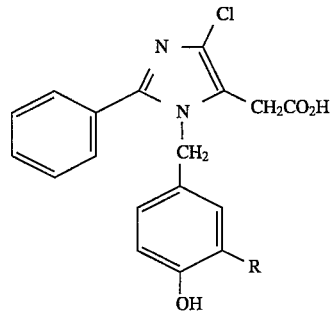

wherein R is lower alkyl. Specifically, the disclosure includes 4-chloro-1-(4-methoxy-3-methylbenzyl)-2-phenylimidazole-5-acetic acid.

European Patent Application 245,637 discloses substituted 4,5,6,7-tetrahydro-1H-imidazo[4,5-c]pyridine derivatives of the formula:

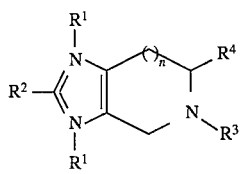

wherein - - - is a single or double bond; one of R¹ is present and includes groups such as $(CH_2)_{1-6}$naphthyl, $(CH_2)_{1-6}$heteroaryl, or $(CH_2)_{1-6}$Ph optionally substituted; R² includes groups such as hydrogen, lower alkyl, and $(CH_2)_{1-5}$Ph; R³ includes groups such as $COC_{1-15}$alkyl or $(CH_2)_{1-6}$Ph optionally substituted; R⁴ includes $CO_2R^9$, wherein R⁹ is hydrogen, lower alkyl or benzyl; and n is 0–3. A compound specifically disclosed is 5-[(4-nitrophenyl)acetyl]-1-(phenylmethyl)-4,5,6,7-tetrahydro-1H-imidazo[4,5-c]pyridine-6-carboxylic acid.

European Patent Application 253,310 discloses substituted 1-aralkylimidazoles having the general formula:

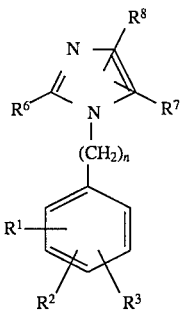

wherein R¹ includes groups such as phenyl optionally substituted or adamantylmethyl; R² includes groups such as hydrogen, halo, $NO_2$, $C_{1-4}$alkyl, or $C_{1-4}$alkoxy; R³ is hydrogen, halo, $C_{1-4}$alkyl, or $C_{1-4}$alkoxy; R⁶ includes groups such as $C_{2-10}$alkyl, $C_{3-10}$alkenyl, $C_{3-8}$cycloalkyl, benzyl optionally substituted or $Z(CH_2)_{1-5}$—R⁵, wherein Z is O or S and R⁵ is $C_{1-6}$alkyl, $C_{3-6}$cycloalkyl or alkenyl; R⁷ is hydrogen, halo, $NO_2$, $CF_3$, or CN, and R⁸ includes groups such as $C_{1-10}$alkanoic acids, esters and amides and alkyl N-alkyl carbamates. Examples include 2-n-butyl-5-chloro-1-(4-nitrobenzyl)imidazole-4-acetic acid and 1-[(2'-carboxybiphenyl-4-yl)methyl]-2-n-butyl-4-chloro-5-(dimethylcarbamoyl) imidazole.

Great Britain Patent 1,341,375 describes a series of substituted imidazoles which are useful due to their activity at H-1, H-2 and/or other histamine receptors. The substituted aminoalkylimidazole compounds disclosed therein are of the formula:

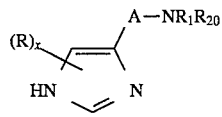

wherein A is $C_{1-6}$ alkyl, optionally substituted by alkyl or aralkyl; R is a substituted or unsubstituted alkyl, aryl or aralkyl group; R₁ is hydrogen alkyl, phenyl, phenylalkyl or imidazolylalkyl; R₂₀ is hydrogen, alkyl optionally substituted by halo, OH, CN, $CO_2H$, $NH_2$ or $CONH_2$; or COY wherein Y is $R_{11}O$ or $R_{11}NH$ and $R_{11}$ is a substituted or unsubstituted alkyl, aryl, aralkyl or amidino group; and X is 0–3. Examples include N-(2-(4(5)-imidazolyl)ethyl)glycine and 1-benzyl-5-(2-aminoethyl)imidazole.

Woolley, et al., *Biochemistry*, 48, 709 (1962) relates to 2-benzylhistidine and derivatives thereof as pilots for the synthesis of peptides designed to have specific enzyme activity. Compounds exemplified in this article include 1,2-dibenzylhistidine and N-carbobenzoxy-1,2-dibenzylhistidine.

DESCRIPTION OF THE INVENTION

The compounds of the present invention that are blockers of angiotensin II receptors are represented by the following Formula (I):

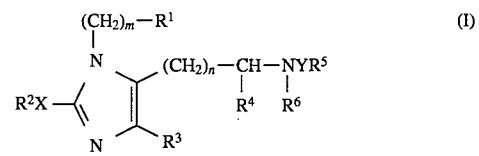

in which:

R¹ is adamantyl, or phenyl, biphenyl, or naphthyl, with each aryl group being unsubstituted or substituted by one to three substituents selected from Cl, Br, F, I, $C_1$–$C_6$alkyl nitro $CO_2R^7$, tetrazol-5-yl, $C_1$–$C_6$alkoxy, hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

R² is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, or $CONR^7R^7$;

X is a single bond, S, or O;

R³ is hydrogen, Cl, Br, F, I, CHO, hydroxymethyl, $COOR^7$, $CONR^7R^7$, $NO_2$, or $C_nF_{2n+1}$;

each n is 1–3;

m is 0–4;

R⁴ is $CO_2$, R⁷, $CONR^7R^7$, or tetrazol-5-yl;

Y is a single bond or a carbonyl group;

R⁵ is hydrogen, $C_1$–$C_8$alkyl, $C_3$–$C_6$cycloalkyl, $(CH_2)_{0-4}$phenyl, or $(CH_2)_{0-3}$CH-diphenyl wherein each phenyl group independently is unsubstituted or substituted by one to three substituents selected from $C_1$–$C_6$alkyl, nitro, Cl, Br, F, I, hydroxy, $C_1$–$C_6$alkyl, $NR^7R^7$, $CO_2R^7$, or $CONR^7R^7$;

R⁶ is hydrogen or $C_{1-6}$alkyl; and each R⁷ independently is hydrogen, $C_1$–$C_4$alkyl, or $(CH_2)_{0-4}$phenyl; or a pharmaceutically acceptable salt thereof.

As used herein, the terms alkyl, alkenyl, alkoxy, and alkynyl mean carbon chains which are branched or unbranched with the length of the chain determined by the descriptor preceding the term.

Preferred compounds of the invention are represented by Formula (I) when:

R¹ is phenyl unsubstituted or substituted by one to three substituents selected from chloro, fluoro, trifluoromethyl, nitro, methyl, methoxy, hydroxy, sulfonamido, cyano, carboxy, carbo$C_1$–$C_4$alkoxy, carbamoyl, or tetrazol-5-yl;

X is a single bond or S;

R² is $C_2$–$C_8$alkyl;

R³ is hydrogen, chloro, fluoro, or trifluoromethyl;

m is 0–2;

R⁴ is $CO_2R_7$; and each R⁷ independently is hydrogen or $C_1$–$C_4$alkyl;

or a pharmaceutically acceptable salt thereof.

Particular compounds of the invention include, but are not limited to, the following:

3-[(2-chlorophenyl)methyl]-2-n-butyl-N-butyrylhistidine,

3-[(2-chlorophenyl)methyl]-2-n-butyl-N-propionylhistidine,

3-[(2-chlorophenyl)methyl]-2-propylthiohistidine,

3-[(2-chlorophenyl)methyl]-2-n-butyl-N-diphenylacetylhistidine,

3-[(2-chlorophenyl)methyl]-2-propylthio-N-[cyclopentyl)carbonyl]histidine,

3-[(2-chlorophenyl)methyl]-2-propylthio-N-acetylhistidine,

3-[(2-chlorophenyl)methyl]-2-propylthio-N-isovalerylhistidine,

3-[(2-chlorophenyl)methyl]-2-propylthio-N-benzoylhistidine, and

3-[(2-chlorophenyl)methyl]-2-propylthiohistidine; or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of treating hypertension, congestive heart failure, renal failure, and glaucoma by administering these compounds are also included in this invention.

The compounds of this invention and of the pharmaceutical compositions and methods of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The following procedures are useful for the preparation of Formula (I) compounds particularly where $R^1$ is 2-chlorophenyl or 4-carboxyphenyl, m is one, $R^2$ is n-propyl or n-butyl, X is S or a single bond, $R^3$ is hydrogen, chloro, fluoro, or trifluoromethyl, $R^4$ is $CO_2H$, $R^6$ is hydrogen, Y is a carbonyl group or a single bond, and $R^5$ is hydrogen, $(CH_2)_{0-2}$phenyl, or CH-diphenyl.

Scheme I

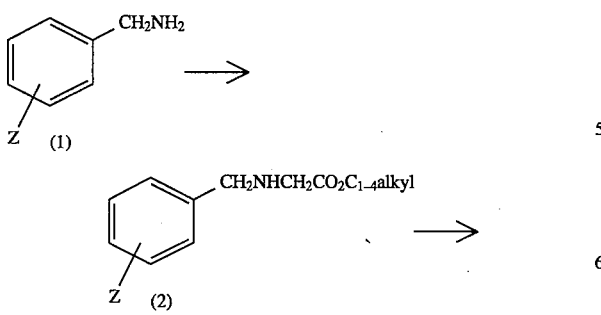

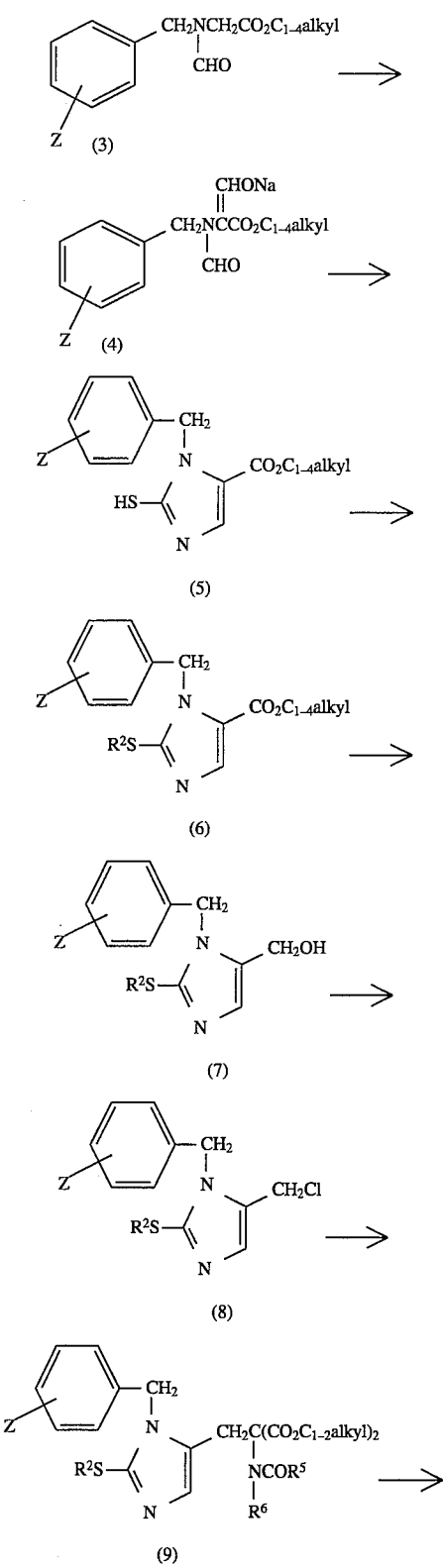

-continued
Scheme I

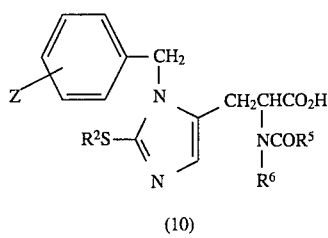
(10)

Scheme I outlines the synthesis of Formula (I) compounds in which the 2-position substituent is $R^2S$. Benzylamines (1), unsubstituted or substituted by one to three Z substituents selected from halo, $C_{1-6}$alkyl, $SO_2C_{1-6}$alkyl, $C_{1-6}$alkoxy, CN, $NO_2$, $CO_2C_{1-4}$alkyl, $SC_{1-6}$alkyl, or $C_nF_{2n+1}$, wherein n is 1–3, are alkylated with a $C_{1-6}$alkyl chloroacetate, for example, methyl chloroacetate, in the presence of a base, such as triethylamine, in a suitable solvent, such as dimethylformamide. The resulting alkylaminoalkyl ester compounds (2) are N-formylated with formic acid in the presence of a suitable solvent, such as xylene, to give formula (3) compounds. Formula (4) compounds are formed by C-formylation of the carbon alpha to both the amino and the ester groups of the formula (3) compounds in a reaction with an alkyl formate, such as methyl formate, in the presence of an alkali metal halide, such as sodium hydride, in a suitable solvent, such as tetrahydrofuran. Reaction of this intermediate with acidic thiocyanate, preferably potassium thiocyanate, in an inert organic solvent, such as $C_{1-4}$alkanol, produces formula (5)1-$R^1CH_2$-2-mercapto-5-alkanoate ester imidazoles. The free thio group of formula (5) compounds is reacted with a halo-$R^8$ compound, wherein $R^8$ is $C_{2-10}$alkyl, $C_{3-10}$alkenyl, $C_{3-6}$cycloalkyl, or an optionally substituted $(CH_2)_{0-8}$phenyl, preferably propyl bromide, in the presence of a suitable base, such as sodium carbonate, in an appropriate solvent, such as ethyl acetate, to give 1-$R^1CH_2$-2-$R^2S$-5-alkanoate ester imidazoles (6). The hydroxymethyl imidazoles of formula (7) are prepared from formula (6) compounds by reduction with an appropriate reagent, such as diisobutyl aluminum hydride, in a suitable solvent, such as tetrahydrofuran, at a temperature of about −78° C. to about 25° C., preferably at about −10° C. The formula (8) chloromethyl compounds are prepared by reacting formula (7) hydroxymethyl compounds with a halogenating agent, such as refluxing thionyl chloride. Reaction of formula (8) compounds with a di$C_{1-2}$alkyl $R^5$-amidomalonate, wherein $R^5$ is as defined for Formula (I) compounds, which had been pre-treated with a deprotonating agent, for example, sodium hydride, yielded formula (9) compounds. Optionally, formula (9) compounds, wherein $R^6$ is H, are alkylated with a $C_{1-6}$alkyl halide, such as methyl iodide, to give the formula (9) compounds, wherein $R^6$ is $C_{1-6}$alkyl. Formula (10) compounds which are Formula (I) compounds, are prepared from formula (9) ester compounds using aqueous base, such as aqueous sodium carbonate solution, in a suitable organic solvent, such as methanol or ethanol.

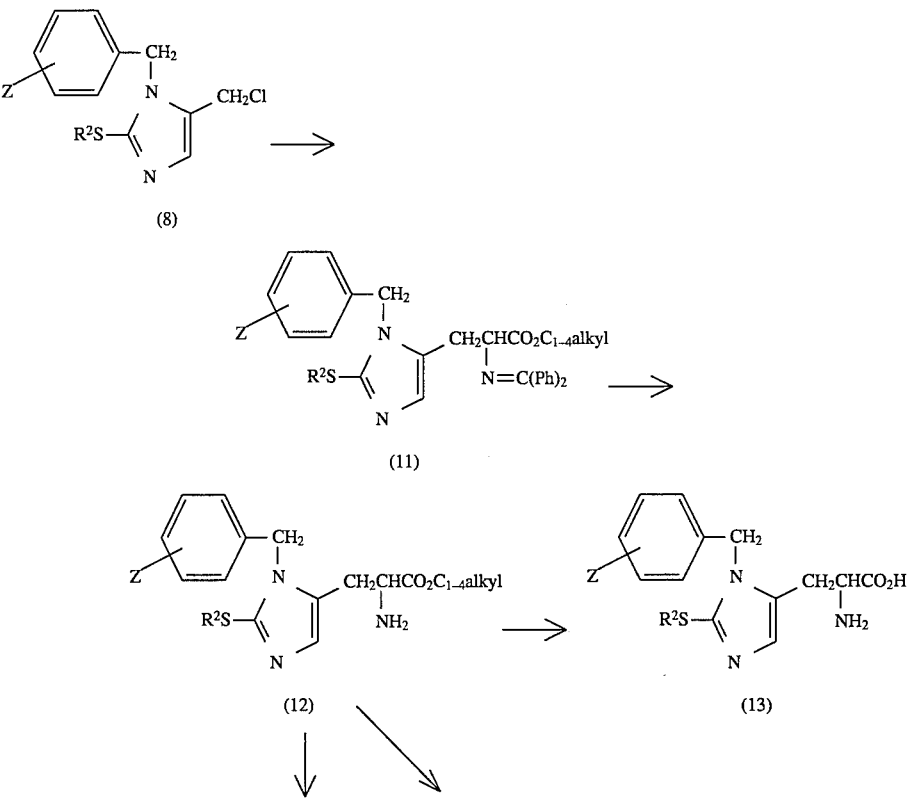

-continued
Scheme II

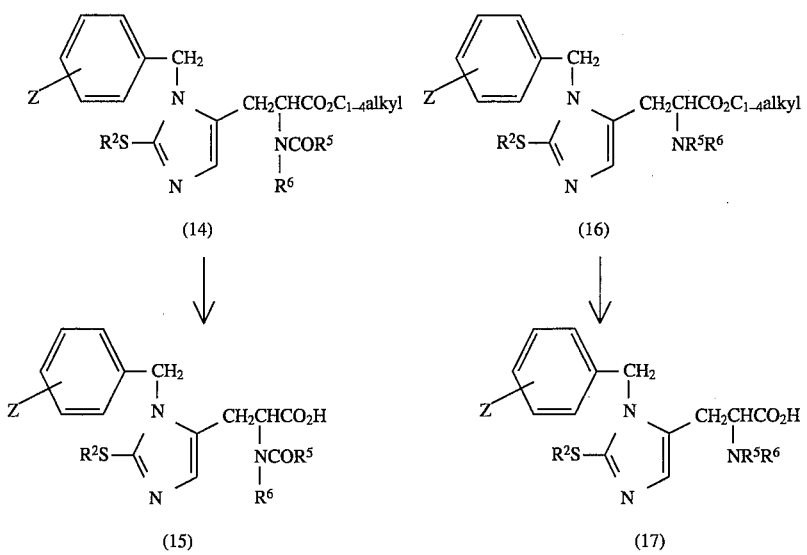

Scheme II depicts an alternate route to Formula (I) compounds. According to Scheme II, chloromethyl imidazoles of formula (8) are converted to formula (11) compounds in a reaction with a N-diphenylmethylene glycine $C_{1-4}$alkyl ester in the presence of a base, such as lithium diisopropylamide, in a suitable solvent, such as tetrahydrofuran, at a temperature of about −78° C. to about 25° C. preferably at about −10° C. The amine alkyl ester compounds of formula (12) are prepared from formula (11) compounds by hydrolysis with a suitable aqueous acid such as aqueous hydrochloric acid.

Formula (12) compounds, which are Formula (I) compounds, are also useful intermediates in the preparation of other Formula (I) compounds. According to Scheme II, formula (14) amide compounds are prepared by reacting formula (12) amine compounds with an acylating agent $R^5$CO-halo in the presence of a base, such as triethylamine. Alternately, formulae (12) amines are monoalkylated by reacting said amines with an appropriately substituted aldehyde, such as benzaldehyde, in the presence of sodium cyanoborohydride. Optionally, formulae (14) and (16) compounds, wherein $R^6$ is H, are alkylated with a $C_{1-6}$alkyl, such as methyl iodide, to give the formulae (14) and (16) compounds, wherein $R^6$ is $C_{1-6}$alkyl. The ester compounds of formulae (12), (14), and (16) are hydrolyzed to formulae (13), (15), and (17) compounds, for example, using base, such as potassium hydroxide, lithium hydroxide, or sodium hydroxide, in a suitable solvent system, such as aqueous methanol or ethanol. Scheme II, formulae (12), (13), (14), (15), (16), and (17) are Formula (I) compounds.

SCHEME III

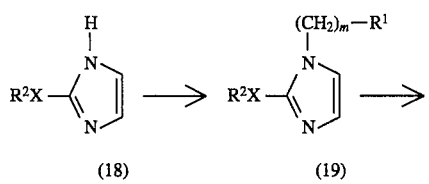

-continued
SCHEME III

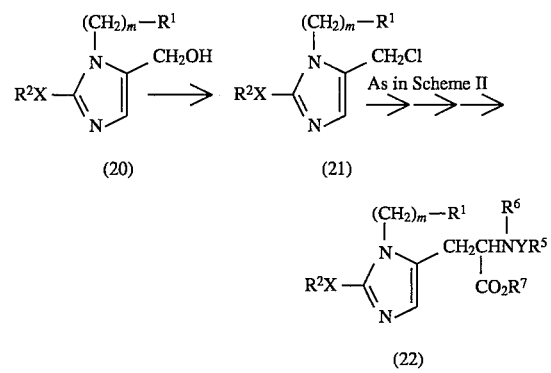

Formula (I) compounds are also prepared by the procedures of Scheme III. The starting 2-$R^2$X-imidazoles of formula (18) are known to the art (*J. Org. Chem.* 45:4038, or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran.

The 1—$R^1(CH_2)_m$-group is incorporated onto the 2—$R^2$X-imidazole of formula (18) by known procedures, for example, by reaction with an $R^1$—$(CH_2)_m$ halide, mesylate or acetate, such as 2-chlorobenzyl bromide, in a suitable solvent, such as dimethylformamide, in the presence of a suitable acid acceptor, such as sodium alkylate, potassium or sodium carbonate, or a metal hydride, preferably sodium hydride, at a reaction temperature of about 25° C. to about 100° C., preferably at about 50° C. The resulting formula (19) imidazole is hydroxymethylated in the 5-position, for example, by reacting with formaldehyde in the presence of sodium acetate in acetic acid to provide the 1—$R^1(CH_2)_m$—2—$R^2$X—5-hydroxymethylimidazole intermediates of formula (20). Chloromethyl formula (21) compounds are prepared from formula (20) these hydroxymethyl-imidazoles in a reaction with a halogenating agent, for example, refluxing thionyl chloride. Formula (I) compounds are prepared from the chloromethyl imidazoles by the methods described in Scheme II.

Alternatively, the 1—$R^1(CH_2)_m$—2—$R^2X$—5-hydroxymethylimidazole intermediates of formula (20) are prepared by reacting an imido ether, $R^2X$—C(=NH)—O-alkyl, such as valeramidine methyl ether, or an amidine, such as valeramidine, with dihydroxyacetone in liquid ammonia under pressure to give 2—$R^2X$—5-hydroxymethylimidazole. This intermediate is reacted with acetic anhydride to give 1-acetyl-5-acetoxymethyl—2—$R^2X$—imidazole. The diacetate intermediate is N-alkylated, for example, using 2-chlorobenzyl triflate and the resulting 1—$R^1(CH_2)_m$—2—$R^2X$—5—acetoxymethylimidazole is treated with aqueous base, such as 10% sodium hydroxide solution, to give the 1—$R^1(CH_2)_m$—$2R^2X$—5-hydroxymethylimidazole intermediate of formula (20). Formula (I) compounds are prepared from the hydroxymethylimidazoles by the procedures detailed above.

Formula (I) compounds wherein the alkylene bridge at the 5 position of the imidazole ring is defined as n equal to 2 or 3 are prepared from the corresponding alkanoic esters, which are disclosed in U.S. Pat. No. 4,340,598, employing the methods hereinbefore described.

Compounds of Formula (I) in which the $R^1$ substituent is substituted by hydroxy are formed from Formula (I) compounds in which the $R^1$ group is substituted by $C_1$–$C_4$alkoxy using an ether-cleaving reagent, such as boron tribromide or hydrobromic acid.

Compounds of Formula (I) in which the $R^1$ substituent is substituted by carboxy are formed from Formula (I) compounds in which the $R^1$ group is substituted by $CO_2C_1$–$C_4$alkyl using basic hydrolysis, such as aqueous sodium or potassium hydroxide in methanol or ethanol, or using acidic hydrolysis, such as aqueous hydrochloric acid.

Compounds of Formula (I) in which the $R^1$ substituent is substituted by a tetrazol-5-yl group are prepared by the methods described in U.S. Pat. No. 4,820,843.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) which have an acidic group are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention is about 1.0 to about 70 µm.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) of compounds of the invention is about 0.05 to about 50 µM.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 3 to 300 mg/kg. The dose of compound needed to produce 50% inhibition of the control response to angiotensin II ($IC_{50}$) is used to estimate the potency of the compounds. The $IC_{50}$ of 3-[(2-chlorophenyl)methyl]-2-n-butyl-N-butyrylhistidine is 10 mg/kg i.v.

Antihypertensive activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally.

The intraocular pressure lowering effects employed in this invention may be measured by the procedure described by Watkins, et al., *J. Ocular Pharmacol.*, 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–200 mg/kg of active compound, preferably 1–100 mg/kg. The selected dose is administered to a human patient in need of angiotensin II receptor antagonism from 1–6 times daily, orally, rectally, topically, by injection, or continuously by infusion. Oral dosage units for human administration preferably contain from 1 to 500 mg of active compound. Lower dosages are used generally for parenteral administration. Oral administration, is used when safe, effective and convenient for the patient. Topical formulations contain the active compound in an amount selected from 0.0001 to 0.1 (w/v%), preferably from 0.0001 to 0.01. As a topical dosage unit form, an amount of active compound from between 50 ng to 0.05 mg, preferably 50 ng to 5 mg, is applied to the human eye.

The method of this invention of antagonizing angiotensin II receptors in mammals, including humans, comprises administering to a subject in need of such antagonism an effective amount of a compound of Formula (I). The method of this invention of producing antihypertensive activity and the method of treating congestive heart failure, glaucoma, and renal failure comprise administering a compound of Formula (I) to a subject in need thereof an effective amount to produce said activity.

The following examples illustrate preparation of compounds and pharmaceutical compositions of this invention. The examples are not intended to limit the scope of this invention as defined hereinabove and as claimed below.

EXAMPLE 1

3-[(2-Chlorophenyl)methyl]-2-propylthio-N-acetylhistidine (i) 5-carboxymethyl-1-(2-chlorophenyl)methyl-2-thio-1H-imidazole A solution of 2-chlorobenzylamine (14.2 g, 0.1 mol) and triethylamine (13.9 mL, 0.1 mol) in dimethylformamide (100 mL) was treated with methyl chloroacetate (10.9 g, 0.1 mol). The mixture was heated at 50° C. for 3.5 hours. The cooled reaction mixture was diluted with diethyl ether, the solids filtered and the concentrated filtrate was flash chromatographed over silica gel with 6:4 hexane in ethyl acetate to provide 15.3 g (71%) of homogeneous methyl 2-[N-(2-chlorophenyl)methyl]aminoacetate. This product (15.2 g, 0.071 mol) in xylene (100 mL) was treated with 98% formic acid (2.74 mL, 0.0711 mol) and the mixture was refluxed for 2.5 hours with a Dean-Stark water separator. Evaporation gave 17.1 g (99%) of methyl 2-[N-(2-chlorophenyl)methyl-N-formyl]aminoacetate. This formylated product (17.0 g, 0.071 mol) was dissolved in methyl formate (13.3 mL, 0.216 mol) and added dropwise to a sodium methoxide mixture prepared by adding sodium metal (1.79 g, 0.0778 g-atom) to tetrahydrofuran (325 mL) followed by slow addition of methanol (3.15 mL, 0.0778 mol). The combined mixture was stirred at room temperature for 18 hours, then evaporated to dryness. This crude product was dissolved in 50% aqueous methanol (200 mL), treated with charcoal, filtered and the solution was cooled in ice. Concentrated hydrochloric acid (14.3 mL of 12N, 0.171 mol) was added slowly to this solution followed by a solution of potassium thiocyanate (8.6 g, 0.0885 mol) in water (20mL). The mixture was heated in an oil bath held at 90° C. for 2.5 hours, then cooled to −10° C. The precipitated solid was filtered, washed with cold ethanol-water and dried at 60° C. to provide 14.7 g (74%) of 5-carboxymethyl-1-1-(2-chlorophenyl)methyl-2-thio-1H-imidazole; m.p. 72°–74° C.

(ii) 1-(2-chlorophenyl)methyl-5-hydroxymethyl-2-propylthio-1H-imidazole

A mixture of 5-carboxymethyl-1-(2-chlorophenyl)-methyl-2-thio-1H-imidazole (2 g, 7.08 mmol), ethyl acetate (20 mL), 5% sodium carbonate solution (40 mL) and propylbromide (4 mL, 44 mmol) was heated at 60° C. for 18 hours. The organic layer was separated, dried over magnesium sulfate and concentrated to 2.23 g of crude product. Trituration with diethyl ether provided 1.63 g (71%) of 5-carboxymethyl-1-(2-chlorophenyl)methyl-2-thiopropyl-1H-imidazole; m.p. 68°–71° C. (from hexane).

The ester was hydrolyzed with aqueous sodium hydroxide solution to give 1-(2-chlorophenyl)methyl-2-thio-propyl-1H-imidazole-5-carboxylic acid; m.p. 158°–159.5° C. (from ethanol).

A solution of 5-carboxymethyl-1-1-(2-chloro-phenyl)-methyl-2-propylthio-1H-imidazole (3.74 g, 11.5 mmol) in dry tetrahydrofuran (50 mL) was cooled to −78° C. under argon, and a solution of diisobutyl aluminum hydride in toluene (30 mL of 1 M) was added dropwise. The mixture was stirred at −78° C. for 1.5 hours, then allowed to slowly warm to room temperature. The reaction was quenched by pouring onto iced dilute acetic acid, the product was extracted into methylene chloride and the organic extracts were washed with water, 5% sodium carbonate solution and brine. The dried, concentrated product was a light tan solid (3.32 g). Crystallization from ethanol/water gave 1-(2-chlorophenyl)-methyl-5-hydroxymethyl-2-propylthio-1H-imidazole; m.p. 98°–101° C.

(iii) 3-(2-chlorobenzenemethyl)-2-propylthio-N-acetylhistidine

A mixture of 1-(2-chlorophenyl)methyl-5-hydroxymethyl-2-propylthio-1H-imidazole (0.117 g, 0.393 mmol) in thionyl chloride (1 mL) was refluxed for 2 hours, evaporated in vacuo to an amorphous solid and triturated with ether to provide 1-(2-chlorophenyl)methyl-5-chloro-methyl-2-thiopropyl-1H-imidazole hydrochloride (0.13 g, 94%).

Crude 1-(2-chlorophenyl)methyl-5-chloromethyl-2-propylthio-1H-imidazole hydrochloride (0.3 g, 0.853 mmole) in dimethyl formamide (2 mL) was added to sodium diethyl acetamidomalonate (prepared by introducing sodium hydride (2.84 mmol) to a solution of diethyl acetamidomalonate (0.415 g, 1.91 mmol) in dimethyl formamide (3mL)). The mixture was stirred under argon at 25° C. for 18 hours, poured into water and the product was extracted into methylene chloride. The water-washed organic extracts were dried and concentrated in vacuo to a light orange product. This crude product was purified over silica gel with 1:1 hexane/ethyl acetate to afford 0.27 g of the malonate addition product. This product was hydrolyzed in 50% aqueous ethanol (20 mL) and sodium carbonate (0.85 g) in water (20 mL) on the steam bath for 3 hours. The reaction mixture was poured into water and extracted with methylene chloride. The washed, dried, concentrated product (0.23 g) was purified by prep TLC on silica gel with a system of 15% methanol in chloroform containing 0.5% of formic acid to provide 0.13 g of 3-[(2-chlorophenyl)methyl]-2-propylthio-N-acetylhistidine as an amorphous solid; m.p. 182°–184° C.

EXAMPLE 2

3-[(2-Chlorophenyl]methyl]-2-propylthio-N-butyrylhistidine (i) 3-[(2-chlorophenyl)methyl]-2-propylthio-histidine ethyl ester A solution of diisopropylamine (8.4 mL) in tetrahydrofuran (100 mL) was cooled to −78° C. under argon and a solution of n-butyl lithium (30 mL of 2.5M in hexane) was added. The mixture was stirred at −78° C. for 30 minutes and at 0° C. for 10 minutes. After being recooled to −78° C., a solution of N-(diphenylmethylene)-glycine ethyl ester (Tetra. Lett., (1978), 2541, 4625) (15.4 g) in tetrahydrofuran (50 mL) was added, the mixture was stirred for 1 hour at −78° C. and a solution of 1-(2-chlorophenyl)methyl-5-chloromethyl-2-propylthio-1H-imidazole hydrochloride (Example 1 (iii)) (9.4 g) in dry dimethylformamide (20 mL) was added. The mixture was then stirred at ambient temperature for 18 hours, poured into saturated ammonium chloride solution and the aqueous layer was extracted with methylene chloride. The organic extracts were washed with water, dried with magnesium sulfate concentrated and chromatographed over silica gel with 1% methanol in methylene chloride to afford 6.88 g of 3-[(2-chlorophenyl)methyl]-2-propylthio-N-(diphenylmethylene)histidine ethyl ester. This product (2.59 g) was dissolved in methylene chloride (52 mL), aqueous 1N hydrochloric acid solution (52 mL) was added and the mixture was stirred at 25° C. for 18 hours. The aqueous layer was separated, neutralized to pH 10.5 with sodium carbonate and the product was extracted into methylene chloride. The organic extract was dried with magnesium sulfate and concentrated to give 1.29 g (71%) of 3-[(2-chlorophenyl)-methyl]-2-propylthiohistidine ethyl ester as an oil.

(ii) 3-[(2-chlorophenyl)methyl]-2-propylthio-N-butyrylhistidine ethyl ester

A solution of 3-(2-chlorophenyl)methyl]-2-propylthiohistidine ethyl ester (0.4 g, 1.05 mmol) in methylene chloride (20 mL) was treated with triethylamine (0.17 mL) and butyryl chloride (0.12 mL). The mixture was stirred at 25° C. for 18 hours. The reaction was partitioned between ethyl acetate and water, and the organic layer was washed with water, dried, concentrated and chromatographed over silica gel with 1 to 3% of methanol in methylene chloride to give 0.367 g (77%) of 3-[(2-chlorophenyl)methyl]-2-propylthio-N-butyrylhistidine ethyl ester as an oil.

(iii) 3-(2-chlorobenzenemethyl)-2-propylthio-N-butyrylhistidine

A mixture of 3-[(2-chlorophenyl)methyl-2-propylthio-N-butyrylhistidine ethyl ester (0.37 g, 0.819 mmole), ethanol (4 mL), water (4 mL) and potassium hydroxide pellets (0.098 g, 1.75 mmole) was stirred at 25° C for 1 hour. The reaction was then diluted with water and the pH was adjusted to 4 with 1N aqueous hydrochloric acid solution. The product was extracted into methylene chloride, washed with water, dried and concentrated to an orange solid. Two crystallizations from chloroform provided 0.22 g of 3-[(2-chlorophenyl)methyl]-2-propylthio-N-butyrylhistidine; m.p. 178°–181° C.

EXAMPLE 3

3-[(2-Chlorophenyl)methyl]-2-propylthio-N-isovalerylhistidine

The procedure of Example 2 (ii-iii) was followed using isovaleryl chloride in place of butyryl chloride to give 3-[(2-chlorophenyl)methyl]-2-propylthiohistidine. The title compound is a white solid obtained in 58% overall yield; m.p. 151°–154° C.

EXAMPLE 4

3-[(2-Chlorophenyl)methyl]-2-propylthio-N-benzoylhistidine

The procedure of Example 2 (ii-iii) was followed using benzoyl chloride in place of butyryl chloride. The title compound is a white solid; m.p. 210°–212° C. (from methanol).

EXAMPLE 5

3-[(2-Chlorophenyl)methyl]-2-propylthio-N-[(cyclopentyl)carbonyl]histidine

The procedure of Example 2 (ii-iii) was followed using cyclopentanecarbonyl chloride in place of butyryl chloride. The title compound is white solid; m.p. 173°–175° C. (from ethanol).

EXAMPLE 6

3-[(2-Chlorophenyl)methyl]-2-propylthio-N-hexanoylhistidine

The procedure of Example 2 (ii-iii) was followed using compound is a white solid; m.p. 118°–121° C. (from ethyl acetate).

EXAMPLE 7

3-[(2-Chlorophenyl)methyl]-2-propylthiohistidine

A solution of 3-[(2-chlorophenyl)methyl]-2propylthiohistidine ethyl ester (Example 2 (i)) (0.48 g, 1.26 mmol), ethanol (4 mL), water (4 mL) and potassium hydroxide (0.111 g, 1.97 mmol) was stirred at 25° C. for 1 hour. The mixture was treated with concentrated hydrochloric acid to pH 4.0 and cooled. The resulting precipitate was collected and triturated with ethanol to give 0.34 g (77%) of 3-[(2-chlorophenyl)methyl]-2-propylthiohistidine; m.p. 227°–228° C.

EXAMPLE 8

3-[(2-Chlorophenyl)methyl]-2-n-butyl-N-butyrylhistidine (i) 2-n-butyl-1-(2-chlorophenyl)methyl-1H-imidazole Imidazole was converted to the 1-diethoxyortho-amide derivative by the method of Curtis and Brown, *J. Org. Chem.*, (1980), 45, 20. Imidazole (12.8 g, 0.19 mol) and 118.4 g (0.8 mol) of triethylorthoformate were reacted in the presence of 1 g of p-toluenesulfonic acid to give 20.6 g (61%), bp 65°–70° C. (0.1 mm) of 1-diethoxyorthoamide imidazole. This product (20.0 g, 0.14 mol) was dissolved in dry tetrahydrofuran (250 mL), cooled to –40° C. and n-butyl lithium (0.14 mol, 56.4 mL of 2.5M in hexane) was added at –40° C. to –35° C. After 15 minutes n-butyl iodide (31.1 g, 0.169 mol) was added at –40° C., and the reaction was stirred overnight at ambient temperature. The reaction was partitioned between ether and 0.3N hydrochloric acid, and the organic layer was repeatedly extracted with dilute hydrochloric acid. The combined aqueous extracts were neutralized with sodium bicarbonate solution, extracted with methylene chloride, dried over magnesium sulfate and concentrated. A flash distillation on a Kugelrohr apparatus provided 14.8 g (85%) of 2-n-butylimidazole.

2-n-Butylimidazole (9.7 g, 0.078 mol) was dissolved in methanol (50 mL) and added dropwise to a solution of sodium methoxide (from sodium hydride (2.31 g, 0.0934 mol) in methanol (250 mL)). After one hour the solution was evaporated to dryness, and the sodium salt was taken up in dry dimethylformamide (150 mL) and 2-chlorobenzyl bromide (16.3 g, 0.079 mol) was added. The mixture was heated at 50° C. for 17 hours under argon, poured onto ice water and the product was extracted into ethyl acetate. The extract was washed, dried, and concentrated to give 18.5 g of crude product which was chromatographed over silica gel with 2:1 ethyl acetate/hexane to provide 11.9 g (61%) of 2-n-butyl-1-(2-chloro-phenyl)methyl-1H-imidazole as an oil. Thin layer chromatography on silica gel with 4:1 ethyl acetate/hexane gave an $R_f$ value of 0.59.

(ii) 2-n-butyl-1-(2-chlorophenyl)-methyl-5-hydroxymethyl-1H-imidazole

Method 1

A mixture of 2-n-butyl-1-(2-chlorophenyl)methyl-1H-imidazole (95.5 g, 0.384 mol), 37% formaldehyde (500 mL), sodium acetate (80 g) and acetic acid (60 mL) was heated to reflux for 40 hours under argon. The reaction was concentrated in vacuo, and the residue was stirred with 500 mL of 20% sodium hydroxide solution for 4 hours, diluted with water and extracted with methylene chloride. The extract was washed, dried, and concentrated. The crude product (117 g) was flash chromatographed over 600 g of silica gel with a gradient of ethyl acetate to 10% of methanol in ethyl acetate to give 8.3 g of starting material, 24.5 g of a mixture of starting material and product, and 44 g (41%) of 2-n-butyl-1-(2-chlorophenyl)-methyl-5-hydroxymethyl-1H-imidazole; mp 86°–88° C. (from ethyl acetate). Further elution provided the bis (4,5-hydroxymethyl) derivative; mp 138°–140° C. (from ethyl acetate).

Method 2

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3L). The resulting slurry was refluxed with added acetonitrile (1L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxymethylimidazole (253 g, 1.63 mol, 98%).

This crude alcohol (253 g) was treated with acetic anhydride (400 mL) at –15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at –78° C. under argon was added a solution of diisopropyl ethylamine (128 mL, 0.73 mol) and 2-chlorobenzyl alcohol (104 g, 0.72 mol) in methylene chloride (350 mL) over a period of 20 minutes. After being stirred an additional 20 minutes at –78° C., this solution was then treated with 1-acetyl-4-acetoxymethyl-2-n-butylimidazole (146 g, 0.61 mol) dissolved in methylene chloride (300 mL) over a 20-minute interval. The mixture was then stirred at ambient temperature for 18 hours and the solvents were evaporated. The residual 2-n-butyl-5-acetoxymethyl-1-(2-chlorophenyl)methyl-1H-imidazole was used without purification for the hydrolysis of the acetate group.

A solution of crude 2-n-butyl-5-acetoxymethyl-1-(2-chlorophenyl)methyl-1H-imidazole (250 g) in methanol (200 mL) was treated with 10% sodium hydroxide solution (700 mL) and the mixture was heated on a steam bath for 4 hours. After cooling, methylene chloride was added, the organic phase was separated, washed with water, dried and concentrated. The residue was dissolved in ether, cooled, and seeded to give the crude product. Recrystallization from ethyl acetate gave 176 g of 2-n-butyl-1-(2-chloro-phenyl)methyl-5-hydroxymethyl-1H-imidazole; mp 86°–88° C. This material was identical in all respects to the product prepared by Method 1.

(iii) 3-[(2-chlorophenyl)methyl]-2-n-butyl-histidine ethyl ester

A mixture of 2-n-butyl-1-(2-chlorophenyl)methyl-5-hydroxymethyl-1H-imidazole (1 g) was refluxed with thionyl chloride (20 mL) for 2 hours. The reaction mixture was evaporated in vacuo and the residue was triturated with diethyl ether to give 1.08 g of 2-n-butyl-1-(2-chlorophenyl)methyl-5-chloromethyl-1H-imidazole hydrochloride.

(iv) 3-[(2-chlorophenyl)methyl]-2-n-butyl-N-butyrylhistidine

The procedure of Example 2 (ii-iii) was followed using 2-n-butyl-3-(2-chlorophenyl)methylhistidine ethyl ester in place of 3-[(2-chlorophenyl)methyl]-2-propylthio-histidine. The title compound is a white solid obtained in 74% overall yield; m.p. 199°–201° C. (from ethyl acetate).

EXAMPLE 9

3-[(2-Chlorophenyl)methyl]-2-n-butyl-N-propionylhistidine

The procedure of Example 8 was followed using propionyl chloride in place of butyryl chloride to give 2-n-butyl-3-(2-chlorophenyl)methylhistidine ethyl ester. The title compound is a white solid; m.p. 203°–205° C. (from ethyl acetate/hexane).

EXAMPLE 10

3-[(2-Chlorophenyl)methyl]-2-n-butyl-N-diphenylacetylhistidine

The procedure of Example 8 was followed using diphenylacetyl chloride in place of butyryl chloride to give 2-n-butyl-3-(2-chlorophenyl)methylhistidine. The title compound is a white powder; m.p. 222°–225° C. (from methanol).

EXAMPLE 11

3-[(2-Chlorophenyl)methyl]-2-n-butyl-N-3-phenylpropionylhistidine

The procedure of Example 8 was followed using 3-phenylpropionyl chloride in place of butyryl chloride to give 2-n-butyl-3-(2-chlorophenyl)methylhistidine. After trituration with cyclohexane, the title compound (as the hydrochloride salt) is a white solid; m.p. 194°–196° C.

EXAMPLE 12

3-[(2-Chlorophenyl)methyl]-2-n-butyl-N-(phenylacetyl)histidine

The title compound is prepared according to Example 8 using phenylacetyl chloride in place of butyl chloride.

EXAMPLE 13

3-[2-Chlorophenyl)methyl]-2-n-butyl-N-benzylhistidine

The title compound is prepared by reductive alkylation of 2-n-butyl-3-(2-chlorophenyl)methylhistidine ethyl ester with benzaldehyde in the presence of sodium cyanoborohydride to give 3-[(2-chlorophenyl)methyl]-2-n-butyl-N-benzylhistidine ethyl ester. Hydrolysis of the ester group is accomplished according to Example 2 (iii) to provide the title compound.

EXAMPLE 14

3-[(2-Chlorophenyl)methyl]-2-n-butyl-N-benzyl-N-methylhistidine

3-[(2-chlorophenyl)methyl]-2-n-butyl-N-benzylhistidine (prepared in Example 13) is reacted with methyl iodide to give the title compound.

EXAMPLE 15

The following compounds are prepared by the procedures hereinbefore described:

3-[(4-carboxyphenyl)methyl]-2-n-butyl-N-butyrylhistidine,

3-[(4-carboxy-2-chlorophenyl)methyl]-2-n-butyl-N-butyrylhistidine,

3-[(4-carboxy-3-chlorophenyl)methyl]-2-n-butyl-N-butyrylhistidine,

3-[(4-carboxy-2,3-dichlorophenyl)methyl]-2-n-butyl-N-butyrylhistidine,

3-[(4-carboxyphenyl)methyl]-2-(1-butenyl)-N-butyrylhistidine,

3-[(4-carboxyphenyl-3-trifluoromethylphenyl)methyl]-2-n-butyl)-N-butyrylhistidine, 3-[(4-carboxyphenyl)methyl]-2-n-propyl-N-butyrylhistidine, 3-[(4-carboxyphenyl)methyl]-2-n-hexyl-N-butyrylhistidine, 3-[(4-carboxy-2-nitrophenyl)methyl]-2-n-butyl-N-butyrylhistidine, 3-[(4-nitrophenyl)methyl]-2-n-butyl-N-butyrylhistidine, and 3-[(4-[1H-tetrazol-5-yl]phenyl)methyl]-2-n-butyl-N-butyrylhistidine.

EXAMPLE 16

An oral dosage form for administering orally active Formula (I) compounds is produced by screening, mixing and filling into hard gelatin capsules the ingredients in proportions, for example, as shown below.

| Ingredients | Amounts |
| --- | --- |
| 3-[(2-chlorophenyl)methyl]-2-n-butyl-N-butyrylhistidine | 100 mg |
| magnesium stearate | 10 mg |
| lactose | 100 mg |

EXAMPLE 17

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| 3-[(2-chlorophenyl)methyl]-2-n-butyl-N-propionylhistidine | 75 mg |
| calcium sulfate dihydrate | 100 mg |
| sucrose | 15 mg |
| starch | 8 mg |
| talc | 4 mg |
| stearic acid | 2 mg |

EXAMPLE 18

3-[(2-chlorophenyl)methyl]-2-n-butyl-N-butyrylhistidine, 50 mg, is dispersed in 25 ml of normal saline to prepare an injectable preparation.

EXAMPLE 19

A topical opthalmological solution for administering Formula (I) compounds is produced by mixing under sterile conditions the ingredients in proportions, for example, as shown below.

| Ingredients | Amounts |
| --- | --- |
| 3-[(2-chlorophenyl)methyl]-2-propylthio-N-butyrylhistidine | 1.0 mg |
| dibasic sodium phosphate | 10.4 mg |
| monobasic sodium phosphate | 2.4 mg |
| chlorobutanol | 5.0 mg |
| hydroxypropanol methylcellulose | 5.0 mg |
| sterile water | q.s. ad 1.0 mL |
| 1.0 N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. A method of antagonizing angiotensin II receptors in mammals which comprises administering to a subject in need thereof an effective amount of a compound of formula (I):

$$\begin{array}{c}(CH_2)_m-R^1\\|\\N\\R^2X-\!\!\!\!\diagup\!\!\diagdown\!\!\!\!\!\diagdown(CH_2)_n-CH-NYR^5\\|\quad\quad\quad|\\R^4\quad R^6\\N\quad R^3\end{array}\quad (I)$$

in which:

$R^1$ is adamantyl, or phenyl, biphenyl, or naphthyl, with each aryl group being unsubstituted or substituted by one to three substituents selected from Cl, Br, F, I, $C_1$–$C_6$alkyl, nitro, $CO_2R^7$, tetrazol-5-yl, $C_1$–$C_6$alkoxy, hydroxy, $SC_1$–$C_6$ alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy $C_1$–$C_6$alkoxy $NR^7R^7$ $CO_2R^7$, CN or $CONR^7R^7$;

X is a single bond, S, or O;

$R^3$ is hydrogen, Cl, Br, F, I, CHO, hydroxymethyl, $COOR^7$ $CONR7R^7$ $NO_2$, or $C_nF_{2n+1}$;

each n is 1–3;

m is 0–4;

$R^4$ is $CO_2R^7$, $CONR^7R^7$, tetrazol-5-yl;

Y is a single bond or a carbonyl group;

$R^5$ is hydrogen, $C_1$–$C_8$alkyl, $C_3$–$C_6$cycloalkyl, $(CH_2)_{0-4}$phenyl, or $(CH_2)_{0-3}$CH—diphenyl wherein each phenyl group independently is unsubstituted or substituted by one to three substituents selected from $C_1$–$C_6$alkyl, nitro, Cl, Br, F, I, hydroxy, $C_1$–$C_6$alkyl, $NR^7R^7$, $CO_2R^7$, or $CONR^7R^7$;

$R^6$ is hydrogen or $C_{1-6}$alkyl; and each $R^7$ independently is hydrogen, $C_1$–$C_4$alkyl, or $(CH_2)_{0-4}$phenyl; or a pharmaceutically acceptable salt thereof.

2. A method of claim 1 wherein the compound is 3-[(2-chlorophenyl)methyl]-2-n-butyl-N-butyrylhistidine.

3. A method of claim 1 wherein the compound is 3-[(2-chlorophenyl)methyl]-2-n-butyl-N-propionylhistidine.

4. A method of claim 1 wherein the compound is 3-[(2-chlorophenyl)methyl]-2-propylthio-N-butyrylhistidine.

5. A method of claim 1 wherein the compound is:

3-[(2-chlorophenyl)methyl]-2-n-butyl-N-diphenylacetylhistidine;

3-[(2-chlorophenyl)methyl]-2-propylthio-N-[(cyclopentyl)carbonyl]histidine;

3-[(2-chlorophenyl)methyl]-2-propylthio-N-acetylhistidine;

3-[(2-chlorophenyl)methyl]-2-propylthio-N-isovalerylhistidine;

3-[(2-chlorophenyl)methyl]-2-propylthio-N-benzoylhistidine; or

3-[(2-chlorophenyl)methyl]-2-propylthiohistidine.

6. A method of treating congestive heart failure in mammals which comprises administering to a subject in need thereof an effective amount of a compound of formula (I):

$$\begin{array}{c}(CH_2)_m-R^1\\|\\N\\R^2X-\!\!\!\!\diagup\!\!\diagdown\!\!\!\!\!\diagdown(CH_2)_n-CH-NYR^5\\|\quad\quad\quad|\\R^4\quad R^6\\N\quad R^3\end{array}\quad (I)$$

in which;

$R^1$ is adamantyl, or phenyl, biphenyl, or naphthyl, with each aryl group being unsubstituted or substituted by one to three substituents selected from Cl, Br, F, I, $C_1$–$C_6$alkyl, nitro, $CO_2R^7$, tetrazol-5-yl, $C_1$–$C_6$alkoxy, hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl $C_3$–$C_6$cycloalkyl, or $(CH_2)_{0[}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, or $CONR^7R^7$;

X is a single bond, S, or O;

$R^3$ is hydrogen, Cl, Br, F, I, CHO, hydroxymethyl, $COOR^7$, $CONR^7R^7$, $NO_2$, or $C_nF_{2n+1}$;

each n is 1–3;

m is 0–4;

$R^4$ is $CO_2R^7$, $CONR^7R^7$, or tetrazol-5-yl;

Y is a single bond or a carbonyl group;

$R^5$ is hydrogen, $C_1$–$C_8$alkyl, $C_3$–$C_6$cycloalkyl, $(CH_2)$ o-phenyl, or $(CH_2)_0$·CH–diphenyl wherein each phenyl group independently is unsubstituted or substituted by one to three substituents selected from $C_1$–$C_6$alkyl, nitro, Cl, Br, F, I, hydroxy, $C_1$–$C_6$alkyl, $NR^7R^7$, $CO_2R^7$, or $CONR^7R^7$;

$R^6$ is hydrogen or $C_{1-6}$alkyl; and each $R^7$ independently is hydrogen, $C_1$–$C_4$alkyl, or $(CH_2)_{0-4}$phenyl; or a pharmaceutically acceptable salt thereof.

7. A method of treating renal failure in mammals which comprises administering to a subject in need thereof an effective amount of a compound of formula (I) :

$$\begin{array}{c}(CH_2)_m-R^1\\|\\N\\R^2X-\!\!\!\!\diagup\!\!\diagdown\!\!\!\!\!\diagdown(CH_2)_n-CH-NYR^5\\|\quad\quad\quad|\\R^4\quad R^6\\N\quad R^3\end{array}\quad (I)$$

in which:

$R^1$ is adamantyl, or phenyl, biphenyl, or naphthyl, with each aryl group being unsubstituted or substituted by one to three substituents selected from Cl, Br, F, I, $C_1$–$C_6$alkyl, nitro, $CO_2R^7$, tetrazol-5-yl, $C_1$–$C_6$alkoxy hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl or $(CH_2)_0$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN or $CONR^7R^7$;

X is a single bond, S, or O;

$R^3$ is hydrogen, Cl, Br, F, I, CHO, hydroxymethyl, $COOR^7$, $CONR^7R^7$, $NO_2$, or $C_nF_{2n+1}$;

each n is 1–3;

m is 0–4;

$R^4$ is $CO_2R^7$, $CONR^7R^7$, or tetrazol-5-yl;

Y is a single bond or a carbonyl group;

$R^5$ is hydrogen, $C_1$–$C_8$alkyl, $C_3$–$C_6$-cycloalkyl, $(CH_2)_{0-4}$phenyl, or $(CH_2)_{0-3}$CH–diphenyl wherein each phenyl group independently is unsubstituted or substituted by one to three substituents selected from $C_1$–$C_6$alkyl, nitro, Cl, Br, F, I, hydroxy, $C_1$–$C_6$alkyl, $NR^7R^7$, $CO_2R^7$, or $CONR^7R^7$;

$R^6$ is hydrogen or $C_{1-6}$alkyl; and each $R^7$ independently is hydrogen, $C_1$–$C_4$alkyl, or $(CH_2)_{0-4}$phenyl; or a pharmaceutically acceptable salt thereof.

8. A method of treating glaucoma in mammals which comprises administering to a subject in need thereof an effective amount of a compound of formula (I):

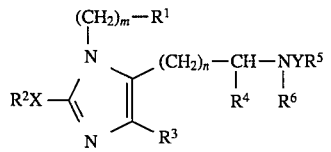

(I)

in which:

$R^1$ is adamantyl, or phenyl, biphenyl, or naphthyl, with each aryl group being unsubstituted or substituted by one to three substituents selected from Cl, Br, F, I, $C_1$–$C_6$alkyl, nitro, $CO_2R^7$, tetrazol-5-yl, $C_1$–$C_6$alkoxy, hydroxy, $SC_1$–$C_6$alkyl, $SO_2NR^7R^7$, $NHSO_2R^7$, $SO_3H$, $CONR^7R^7$, CN, $SO_2C_1$–$C_6$alkyl, or $C_nF_{2n+1}$;

$R^2$ is $C_2$–$C_{10}$alkyl unsubstituted or substituted by $CO_2H$, OH, or $NR^7R^7$, $C_3$–$C_{10}$alkenyl, $C_3$–$C_{10}$alkynyl, $C_3$–$C_6$cycloalkyl or $(CH_2)_0$-phenyl unsubstituted or substituted by one to three substituents selected from $C_1$–$C_6$alkyl, nitro, Cl, Br, F, I, hydroxy, $C_1$–$C_6$alkoxy, $NR^7R^7$ $CO_2R^7$, CN, or $CONR^7R^7$;

X is a single bond, S, or O;

$R^3$ is hydrogen, Cl, Br, F, I, CHO, hydroxymethyl, $COOR^7$, $CONR^7R^7$, $NO_2$, or $C_nF_{2n+1}$;

each n is 1–3;

m is 0–4;

$R^4$ is $CO_2R^7$ $CONR^7R^7$, or tetrazol-5-yl;

Y is a single bond or a carbonyl group;

$R^5$ is hydrogen, $C_1$–$C_8$alkyl, $C_3$–$C_6$cycloalkyl, $(CH_2)_0$-phenyl, or $(CH_2)_0$·CH–diphenyl wherein each phenyl group independently is unsubstituted or substituted by one or three substituents selected from $C_1$–$C_6$alkyl, nitro, Cl, Br, F, I, hydroxy, $C_1$–$C_6$alkyl, $NR^7R^7$, $CO_2R^7$, or $CONR^7R^7$;

$R^6$ is hydrogen or $C_{1-6}$alkyl; and each $R^7$ independently is hydrogen, $C_1$–$C_4$alkyl, or $(CH_2)_{0-4}$phenyl; or a pharmaceutically acceptable salt thereof.

* * * * *